United States Patent
Schwertner et al.

(10) Patent No.: US 10,391,618 B2
(45) Date of Patent: Aug. 27, 2019

(54) PULL-OUT TESTER FOR A SETTING TOOL

(71) Applicant: Hilti Aktiengesellschaft, Schaan (LI)

(72) Inventors: Wolfram Schwertner, Sevelen (CH); Matthias Von Monkiewitsch, Bregenz (AT); Stefan Boenig, Achberg-Esseratsweiler (DE); Peter Bruggmueller, Feldkirch (AT)

(73) Assignee: HILTI AKTIENGESELLSCHAFT, Schaan (LI)

( * ) Notice: Subject to any disclaimer, the term of this patent is extended or adjusted under 35 U.S.C. 154(b) by 350 days.

(21) Appl. No.: 14/443,494

(22) PCT Filed: Dec. 10, 2013

(86) PCT No.: PCT/EP2013/076075
§ 371 (c)(1),
(2) Date: May 18, 2015

(87) PCT Pub. No.: WO2014/090798
PCT Pub. Date: Jun. 19, 2014

(65) Prior Publication Data
US 2015/0328757 A1 Nov. 19, 2015

(30) Foreign Application Priority Data
Dec. 14, 2012 (DE) .................. 10 2012 223 157

(51) Int. Cl.
*B25C 1/18* (2006.01)
*G01N 3/08* (2006.01)

(52) U.S. Cl.
CPC .............. *B25C 1/188* (2013.01); *G01N 3/08* (2013.01); *Y10T 29/49778* (2015.01)

(58) Field of Classification Search
CPC ............. G01N 3/04; G01N 3/08; B25C 5/161
(Continued)

(56) References Cited

U.S. PATENT DOCUMENTS 3,595,072 A * 7/1971 Richards .................. G01N 3/00
                                                           73/803
4,662,227 A * 5/1987 Peterson ............... G01L 5/0033
                                                           73/826
(Continued)

FOREIGN PATENT DOCUMENTS

DE        3841883 A1 * 6/1990 ............. B25B 27/02
DE   196 04 158 A1    8/1997
(Continued)

OTHER PUBLICATIONS

Mathworks: Chudnovsky, "Modeling Flexible Bodies in SimMechanics and Simulink," 2006, <https://www.mathworks.com/company/newsletters/articles/modeling-flexible-bodies-in-simmechanics-and-simulink.html>.*
(Continued)

*Primary Examiner* — Jacob J Cigna
(74) *Attorney, Agent, or Firm* — Leydig Voit & Mayer

(57) ABSTRACT

The invention relates to a pull-out tester (1) for a setting tool used for setting a setting bolt (3), comprising a retaining part (4) for holding the setting bolt (3), an elastic element (7), at least one means (9) for transmitting a pull-out force acting on the setting bolt (3) onto the elastic element (7) such that if a pull-out testing force acting on the setting bolt (3) is exceeded, the connection between the setting bolt (3) and the pull-out tester (1) can be detached due to a deformation of the elastic element (7). The problem addressed by the invention is that of being able to provide a substantially constant pull-out testing force, even in different temperatures and with a different pull-out speed of the pull-out tester (1). The problem is solved in that the force transmitted to the elastic element (7) in order to deform the elastic element (7) substantially causes an elastic deformation of the elastic element (7) and the connection between the setting bolt (3)
(Continued)

Figure 3:
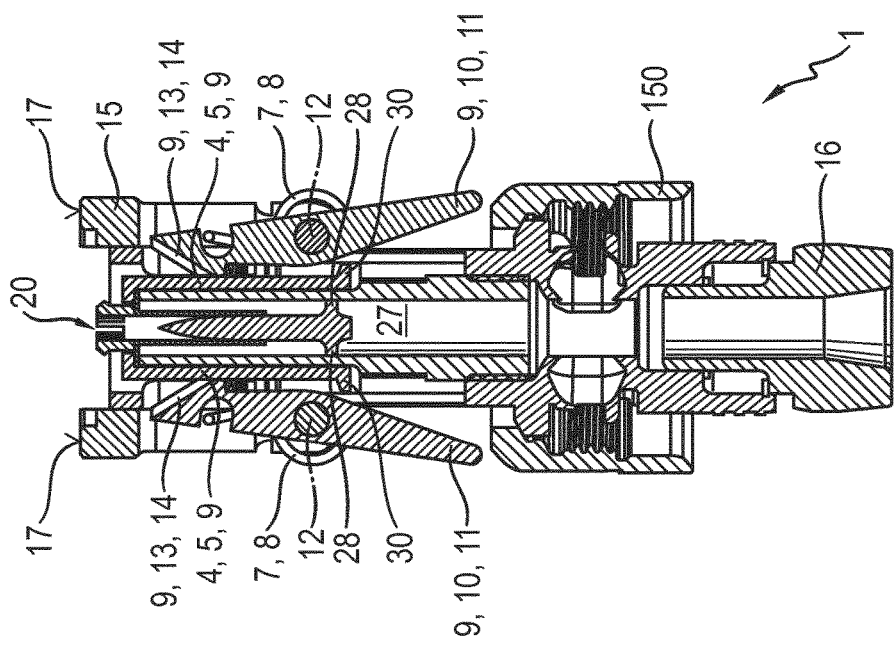

and the pull-out tester (1) can be detached due to the substantially elastic deformation of the elastic element (7).

14 Claims, 5 Drawing Sheets

(58) Field of Classification Search
USPC .......................... 227/63; 73/826, 827, 865.8
See application file for complete search history.

(56) References Cited

U.S. PATENT DOCUMENTS

| | | | | |
|---|---|---|---|---|
| 4,753,115 | A | * | 6/1988 | Moody .................... G01N 3/08 |
| | | | | 73/826 |
| 5,170,922 | A | | 12/1992 | Ehmig et al. |
| 5,703,302 | A | * | 12/1997 | Hasler ....................... B25C 1/02 |
| | | | | 73/826 |
| 6,041,660 | A | * | 3/2000 | Fujitaka ................ G01L 5/0033 |
| | | | | 73/826 |
| 6,393,905 | B1 | * | 5/2002 | Steele .................... G01N 19/04 |
| | | | | 73/150 R |
| 6,891,942 | B1 | | 5/2005 | Porter et al. |
| 7,204,159 | B2 | * | 4/2007 | Hasegawa .............. A41H 37/00 |
| | | | | 73/760 |
| 2008/0257120 | A1 | * | 10/2008 | Tsai ......................... G01N 3/04 |
| | | | | 81/418 |

FOREIGN PATENT DOCUMENTS

| | | | | |
|---|---|---|---|---|
| EP | 1213099 | A2 | 6/2002 | |
| GB | 834293 | A * | 5/1960 | ............. B25C 1/188 |
| GB | 2181087 | A * | 4/1987 | ............. B25C 1/02 |
| GB | 28181087 | A | 4/1987 | |
| JP | H4-226874 | A | 8/1992 | |
| JP | 2010-043939 | A | 2/2010 | |
| KR | 101 087 707 | B1 | 11/2011 | |

OTHER PUBLICATIONS

International Search Report, PCT/EP2013/076075, dated Jun. 5, 2014.

* cited by examiner

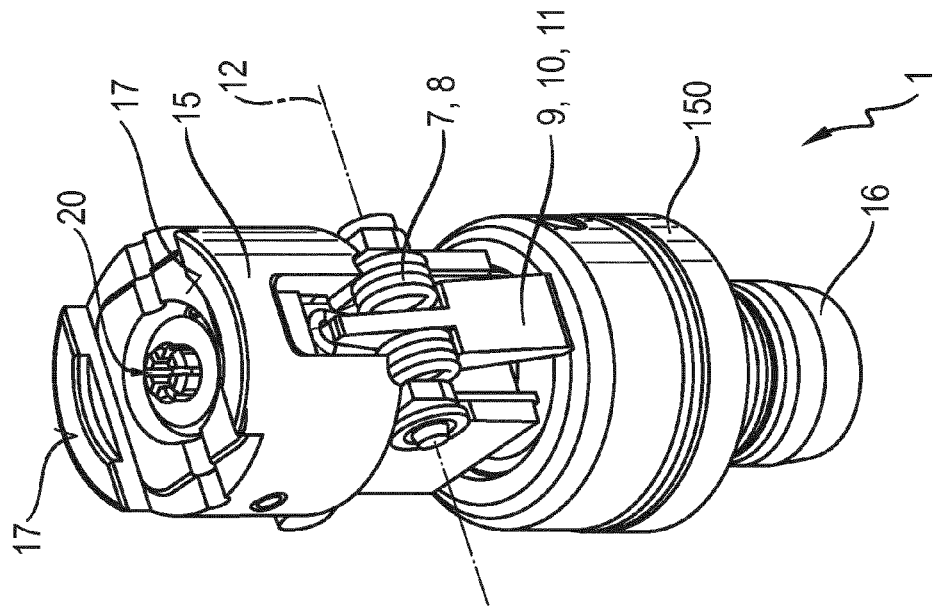
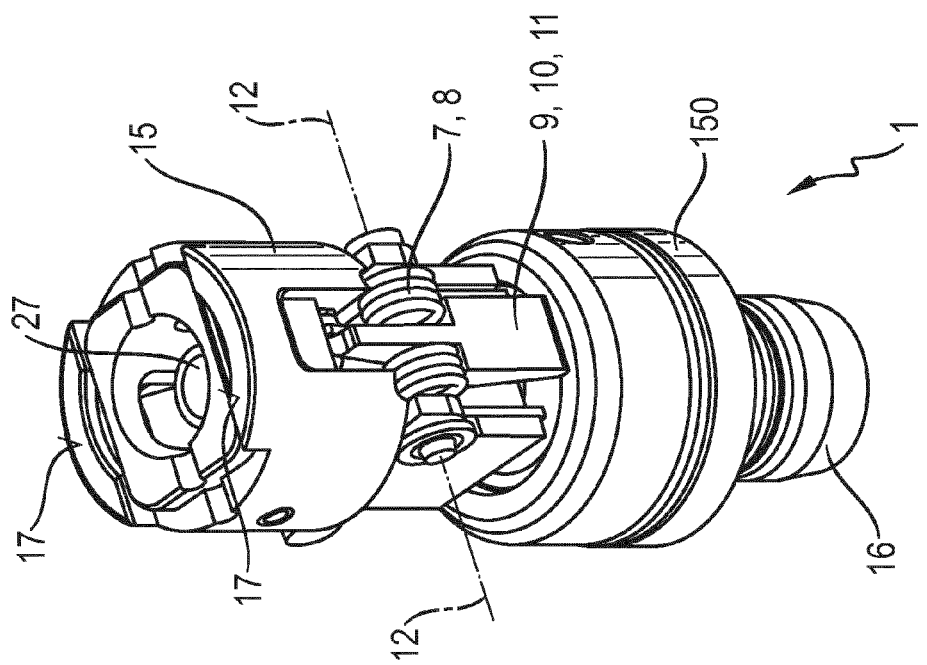

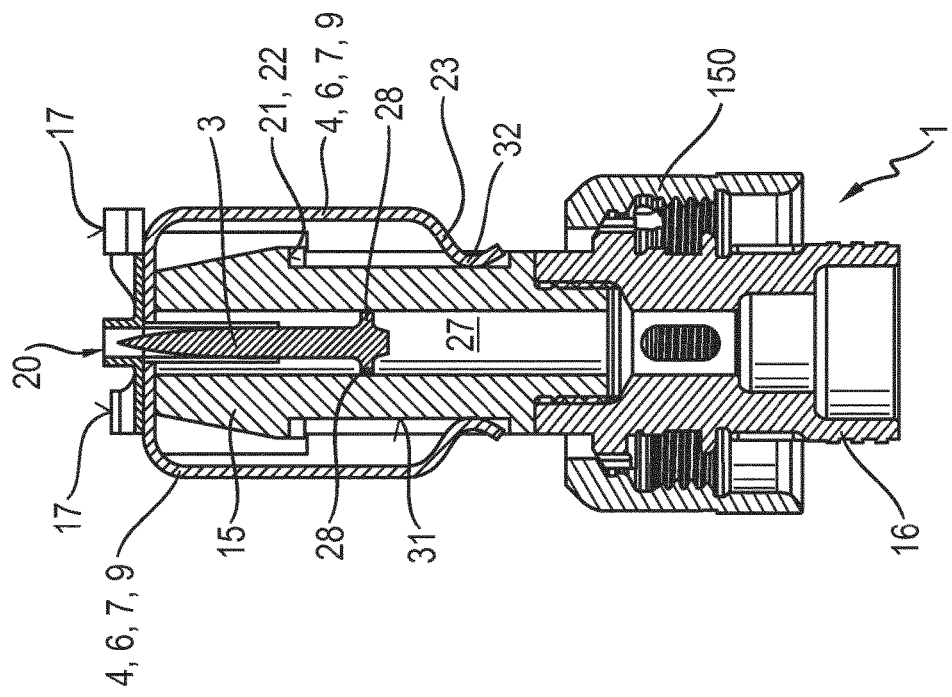
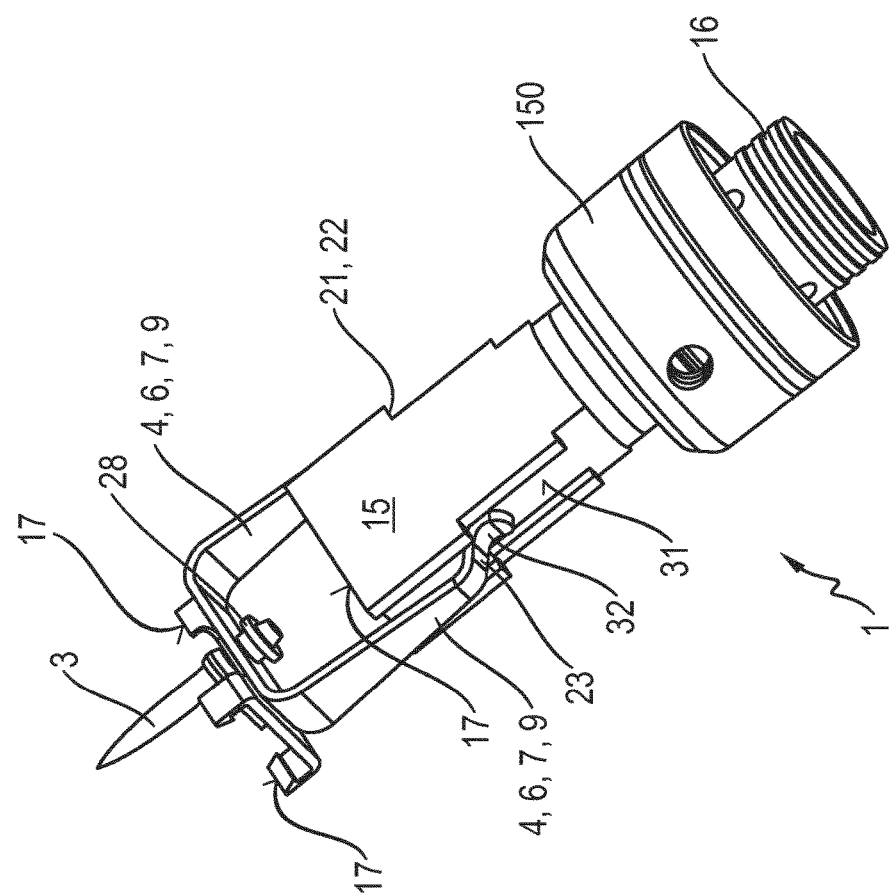

PULL-OUT TESTER FOR A SETTING TOOL

CROSS-REFERENCE TO RELATED APPLICATIONS

The application is the U.S. National Stage of International Application Number PCT/EP2013/076075, filed on Dec. 10, 2013, which claims the benefit of German Patent Application Number 10 2012 223 157.9, filed on Dec. 14, 2012, which are each incorporated by reference.

The invention under consideration concerns a pull-out tester in accordance with the preamble of Claim 1, a setting tool in accordance with the preamble of Claim 9, and a method for the setting of a setting bolt into a setting object in accordance with the preamble of Claim 10.

Setting bolts are inserted into a setting object with a setting tool, so as to be able to fasten a fastening part on the setting object by means of the setting bolt. The fastening part is, for example, a suspended ceiling and the setting object a concrete ceiling. For the fastening of the suspended ceiling on the concrete ceiling in a building, it is necessary to fasten with a setting tool a large number of setting bolts, generally made of metal and particularly steel, on the concrete ceiling. The pull-out forces for the carrying of the suspended ceiling, which can be accepted by the set bolts, vary. There will be obvious and concealed setting failures. With obvious setting failures, it is optically recognizable from the outside that the setting bolts cannot accept sufficient tensile forces. With concealed setting failures, it is generally not possible for the user to see optically from the outside whether the setting bolt can accept a sufficient tensile force for the carrying of the ceiling.

Methods are already known for testing the maximum pull-out force that can be accepted by the set bolts. To this end, the setting bolt is stressed for a tensile force with a pull-out test force and in case of a concealed setting failure, is pulled out again from the concrete ceiling as a result of the pre-specified pull-out force of the setting bolt, and with a setting bolt with a sufficient carrying capacity, the setting bolt also remains within the setting object as the concrete ceiling with the stress with the pull-out test force, so that the setting bolt has a sufficient carrying capacity or a sufficient capacity for the acceptance of tensile forces. To this end, plastic catches that are deformed are used. The plastic catches, however, exhibit a great thermal influence, so that at different temperatures, very different pull-out test forces also appear. The area of the pull-out test force must thereby be selected in such a way, however, that a sufficient pull-out test force is available in all areas. Thus, setting bolts, however, are tested on greater tensile forces with the greater pull-out test forces and, in this way, setting bolts are also pulled out from the concrete ceiling, although they exhibit a sufficient tensile force. A deformation and a tearing of the plastic part or the plastic catch appear, so that the pull-out speed also has an influence on the pull-out test force. The higher the temperature and the slower the pull-out speed, the smaller the pull-out test force. The minimum pull-out test force thus appears with the maximum temperature used and the minimum pull-out speed. With the minimum pull-out test force, however, a sufficient tensile force of the setting bolt must still be available so that at lower temperatures and with greater pull-out speeds, the setting bolts are tested at greater pull-out forces than is required. Thus, more set bolts are classified as setting failures and pulled out of the concrete ceiling than actually required.

The goal of the invention under consideration consists in making available a pull-out tester, a setting tool, and a method for the setting of a setting bolt into a setting object, in which an essentially constant pull-out test force can be made available even at various temperatures and at a different pull-out speed of the pull-out tester.

This goal is attained with a pull-out tester for a testing tool to set a setting bolt, comprising a retaining part to retain the setting bolt, an elastic element, at least one means for the transmission of a pull-out force acting on the setting bolt onto the elastic element, so that with the exceeding of a pull-out test force acting on the setting bolt due to a deformation of the elastic element, the connection between the setting bolt and the pull-out tester is detached, wherein the force for the deformation of the elastic element, transmitted onto the elastic element, essentially causes an elastic deformation of the elastic element and due to the essentially elastic deformation of the elastic element, the connection between the setting bolt and the pull-out tester is detached. Thus, an essentially elastic deformation appears on the elastic element and there is essentially no plastic deformation. The essentially elastic deformation causes the detachment of the connection between the setting bolt and the pull-out tester. In this way, the pull-out test force is essentially constant even at various temperatures and at a different pull-out speed of the pull-out tester. The elastic element is thereby made of a material in which the spring constant of the elastic element is essentially independent of the temperature—that is, at temperatures between −20° C. and +40° C., the spring constant exhibits a variation of less than 20%, 10%, 5%, or 3%. Furthermore, with an elastic element, the speed of the deformation of the elastic element does not have any influence or essentially no influence on the spring constant of the elastic element. Thus, even at various ambient temperatures—that is, at various temperatures and at a different pull-out speed—the essentially similar and constant pull-out test force can be made available by the pull-out tester. The pull-out test force can thus be dimensioned to the extent that at, for example, 0.15 kN, preferably, between 0.05 kN and 0.5 kN, these concealed setting failures on the setting bolt are detected and with forces greater than the essentially constant pull-out force, the connection between the setting bolt and the pull-out tester is detachable or is detached, so that, in this way, the setting bolt remains in the setting object and thus, can be used to accept fastening parts, for example, a suspended ceiling. In this way, advantageously, only those setting bolts are removed from the setting object by the pull-out tester, which cannot accept sufficient tensile forces—that is, in which a concealed setting failure appears.

In another embodiment, the elastic element is designed so that the deformation of the elastic element is, by at least 80%, 90%, and 95%, an elastic deformation.

In a supplementary variant, the elastic element is made, at least partially and in particular, completely, of metal. At various temperatures, metal, for example, iron, has an essentially constant spring constant.

Appropriately, the elastic element is a spring, in particular, a rotational spring or a compression spring, and/or the retaining part is a retaining sleeve.

In an additional embodiment, the retaining part is mechanically connected with at least one transmission part, in particular, a lever, and the retaining force on the retaining part acts on the transmission part, so that by means of a movement, in particular, a swiveling movement, of the transmission part, in particular, the lever, the elastic element is deformable. The setting bolt is fastened, preferably, in a form-locking manner, on the retaining part, in particular, a connecting opening on the retaining part. The tensile force, transmitted from the retaining part to the setting bolt, is transmitted, as the pull-out test force, onto the at least one transmission part, in particular, the lever or a mechanism, for example, with a toothed wheel, so that the tensile force on the setting bolt causes, as a pull-out test force, a movement of the at least one transmission part and movement of the transmission part from the elastic element is prevented, in that the force of the movement, transmitted from the elastic element to the transmission part, is directed in an opposing manner. The greater the tensile force acting on the setting bolt, the greater is the movement of the transmission part and vice-versa. With an exceeding of a limiting position of the transmission part with the pull-out test force, a connection, in particular, a form-locking and/or force-locking connection, is detached as a result of the movement of transmission part. In this way, the connection between the setting bolt and the pull-out tester is detached when the pull-out test force is exceeded.

In a supplementary design, the retaining part with the at least one transmission part is mechanically connected with an at least one connecting part, in particular, two connecting arms, so that the pull-out force can be transmitted from the retaining part to the transmission part with the at least one connecting part, and/or the transmission part and/or the connecting part forms the at least one means for the transmission of a pull-out force acting on the setting bolt onto the elastic element. The transmission part and the connecting part are thus a means for the transmission of the pull-out force acting on the setting bolt onto the elastic element and thus form a mechanism for the transmission of the tensile force on the setting bolt onto the elastic element.

In a supplementary variant, the retaining part forms the elastic element and/or the retaining part forms the at least one means for the transmission of a pull-out force acting on the setting bolt onto the elastic element, and/or the retaining part is designed as an essentially U-shaped retaining clip. The essentially U-shaped retaining clip thus forms a spring as an elastic element. Furthermore, the retaining clip also forms the retaining part for retaining the setting bolt, so that, in this way, the retaining part also forms the means for the transmission of a tensile force acting on the setting bolt onto the elastic element, since it is also this itself.

In a supplementary embodiment, a form-locking configuration, in particular, a projection or a groove, is designed on the remainder of the pull-out tester, on which the retaining part is fastened in a form-locking manner, and with an exceeding of a pull-out test force acting on the retaining part, the form-locking connection between the retaining part and the form-locking configuration is detached as a result of an essentially elastic deformation of the retaining part as an elastic element, in particular, due to the configuration of the retaining part. To this end, the retaining part has, for example, an inclined section and thus, due to this configuration of the retaining part, as a function of the tensile force acting on the setting bolt, a deformation of the retaining part appears, and this deformation is all the greater, the greater the tensile force acting on the setting bolt and vice-versa, so that beyond a specific limiting deformation or limiting position of the retaining part, the connection, in particular, a form-locking and/or force-locking connection, between the retaining part and the form-connecting configuration is detachable or is detached.

Likewise, the goal is attained with a setting tool comprising a housing, a device, for example, a firing pin with a driving means, for example, a pyrotechnical, in particular, a solid, liquid, or gaseous propellant charge, for the firing pin, to introduce a setting bolt into a setting object, an actuation element, for example, a switch, to actuate the device, in particular, the driving means, wherein the setting tool comprises a pull-out tester, as described here, in particular, the pull-out tester on which the remaining setting tool is structured or integrated, and/or a method described here can be carried out.

In an additional embodiment, the driving means is a spring that can be brought under tension by an electric motor in order to move or impact the firing pin or a combustion chamber in order to move or impact the firing pint or a compressed air piston, which can be impinged on so as to move or impact the firing pin.

The method in accordance with the invention for the setting of a setting bolt into a setting object, in particular, with a setting tool described in the patent application, with the steps: the setting of the setting bolt into the setting object, for example, a concrete ceiling, the application of a pull-out testing force on the setting bolt and the pull-out test force is transmitted onto an elastic element, so that the elastic element is elastically deformed, wherein due to the elastic deformation, in particular, an essentially elastic deformation, of the elastic element, a direct or indirect connection, in particular, a form-locking and/or force-locking connection, between the setting bolt and the setting tool is detached with the exceeding of the pull-out test force acting on the setting bolt.

Appropriately, with a pull-out force below the pull-out test force acting on the setting bolt, the connection between the setting bolt and the setting tool is retained.

In an additional embodiment, after the detachment of the connection between the setting bolt and the setting tool from the elastic element, an essentially complete elastic recovery is carried out and/or the elastic element is essentially elastically deformed, in particular, by at least 80%, 90%, or 95% elastically, and/or essentially a plastic deformation is not carried out on the elastic element, for example, less than 20%, 10%, or 5% plastically deformed.

In another development, a spring is deformed, in particular, a rotational spring, as an elastic element and preferably, the spring is made at least in part, in particular, completely, of plastic.

Advantageously, the pull-out test force is transmitted from a retaining part, directly or indirectly, onto a transmission part, in particular, a lever, so that the transmission part is moved, in particular, the lever is swiveled.

In an additional variant, the transmission part is mechanically connected with the elastic element, in particular, the rotational spring, so that due to the movement, in particular, the swiveling of the transmission part, the elastic element is elastically deformed.

Figure 4:
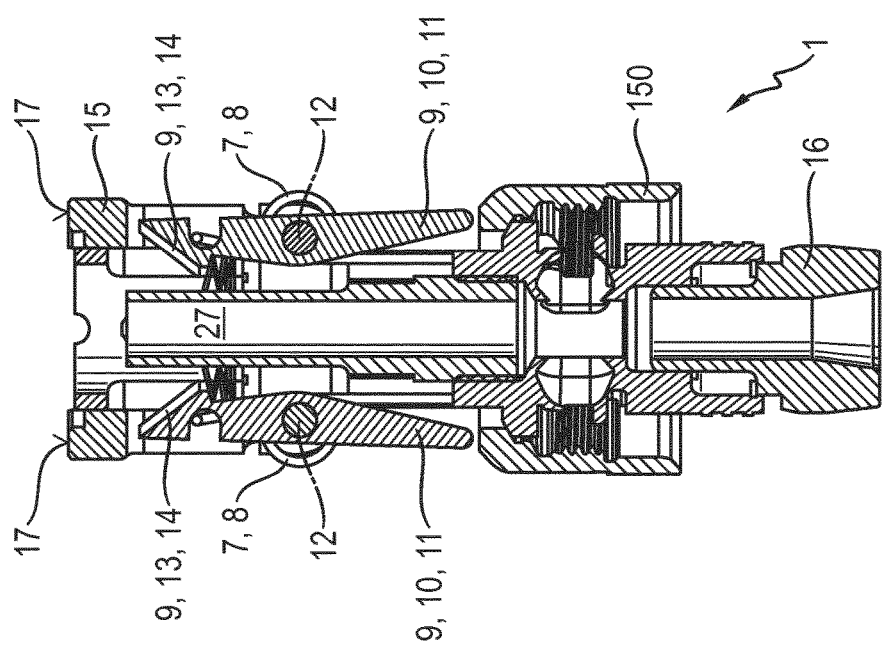
Figures 5, 6:
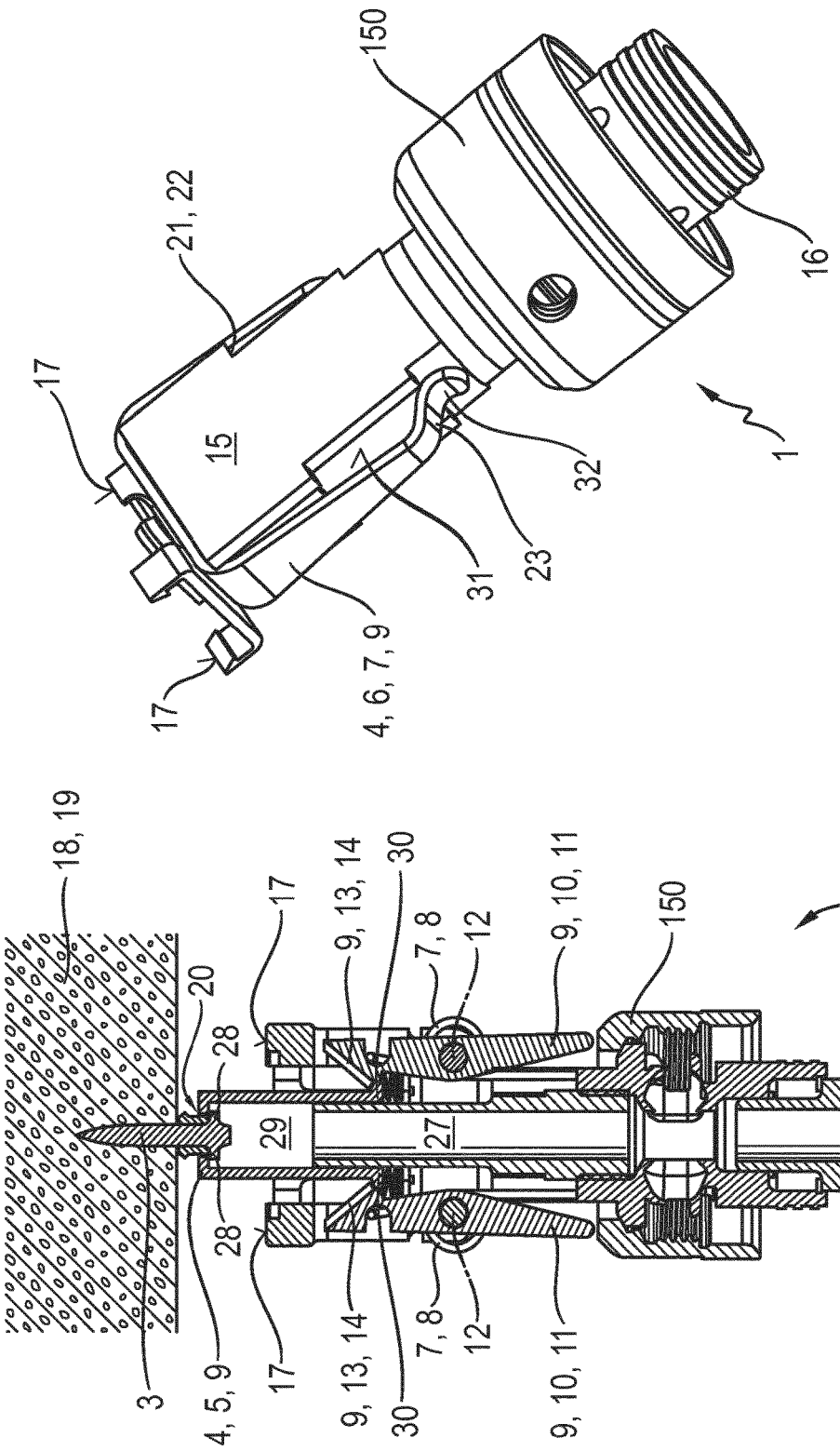
Figure 10:
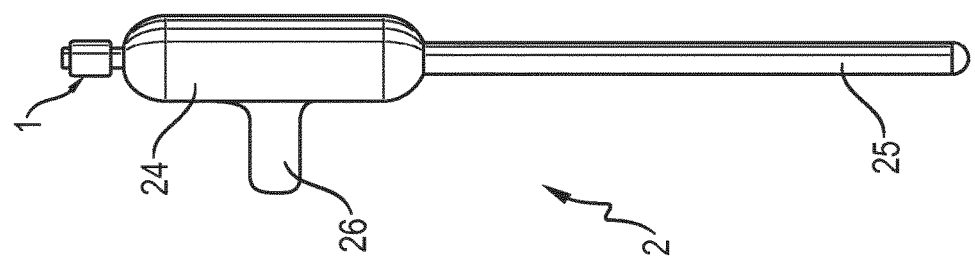
Figure 9:
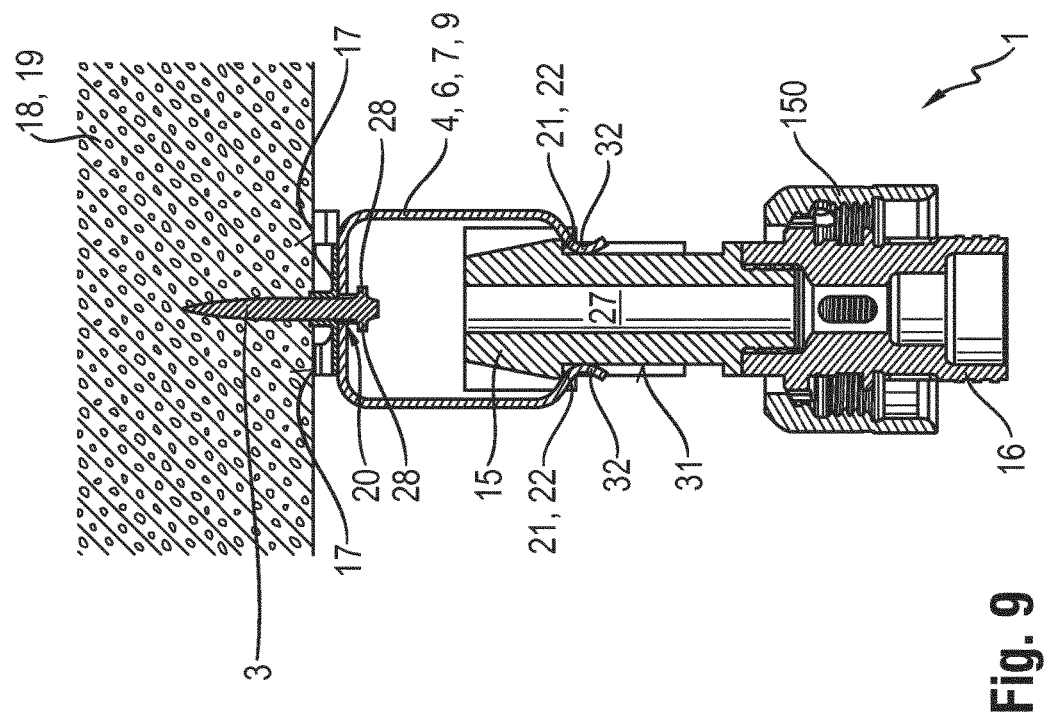

Embodiment examples of the invention are described in more detail in the following with reference to the appended drawings. The figures show the following:

FIG. 1 a perspective view of a pull-out tester in a first embodiment example without a retaining part for a setting bolt;

FIG. 2 a perspective view of the pull-out tester in accordance with FIG. 1 with the retaining part;

FIG. 3 a longitudinal section of the pull-out tester in accordance with FIG. 1 without the retaining part and without the setting bolt;

FIG. 4 a longitudinal section of the pull-out tester in accordance with FIG. 1 with the retaining part and with the setting bolt before the setting of the setting bolt into a setting object;

FIG. 5 a longitudinal section of the pull-out tester in accordance with FIG. 1 with the retaining part and with the setting bolt after the setting of the setting bolt into the setting object;

FIG. 6 a perspective view of the pull-out tester in a second embodiment example with the retaining part before the setting of the setting bolt;

FIG. 7 a perspective view of the pull-out tester in accordance with FIG. 6 with the retaining part after the setting of the setting bolt without a representation of the setting object;

FIG. 8 a longitudinal section of the pull-out tester in accordance with FIG. 6 with the retaining part before the setting of the setting bolt;

FIG. 9 a longitudinal section of the pull-out tester in accordance with FIG. 7 with the retaining part after the setting of the setting bolt and a representation of the setting object; and FIG. 10 a side view of a setting tool with the pull-out tester.

A setting tool 2, shown in FIG. 10, is used to drive in or to set setting bolts 3 or a setting element 3 with the setting tool 2 into a setting object 18, for example, a concrete ceiling 19. To this end, the setting tool 2 has a housing 24, on which a retaining grip 26 is also formed so as to hold the setting tool 2. Within the housing 24 of the setting tool 2, a non-depicted device is formed to introduce or set the setting bolt 3 into the concrete ceiling 19. For example, the device is a firing pin, which is driven by a pyrotechnical propellant charge and, in this way, by means of the firing pin, the setting bolts 3 or the setting element 3 is driven into the setting object 18. The setting bolts 3 are thereby driven into the concrete ceiling 19, so that the setting tool 2 is preferably formed with a retaining rod 25 to retain the setting tool 2 on the concrete ceiling 19. With particular preference, the retaining rod 25 is formed as a trigger rod and transmits a trigger signal, in particular, in a mechanical manner, to the setting tool 2. A pull-out tester 1 is structured or integrated on the setting tool 2.

A first embodiment example of the pull-out tester 1 is shown in FIGS. 1 to 5. The pull-out tester 1 has a pull-out tester housing 15 with a union nut 150 made of metal or plastic and a piston brake 16, dampening the forward movement of a setting piston, for the connection of the pull-out tester 1 with the setting tool 2 or the remainder of the setting tool 2. On a first axial end of the pull-out tester 1, this has a stop 17 for the placing on the concrete ceiling 19 or an additional part of the fastening element to be set and the piston brake 16 is formed on a second axial end of the pull-out tester 1. The pull-out tester housing 15 has a bolt chamber 27 to accept the setting bolt 3, which is fastened as a retaining sleeve 5 on a retaining part 4.

The pull-out tester 1 without the setting bolt 3 and without the retaining sleeve 5 is shown in FIGS. 1 and 3. The setting bolt 3 on the retaining sleeve 5 is introduced into the bolt chamber 27 in FIG. 4, so that, in this way, by means of the setting tool 2, the setting bolt 3 can be set into the concrete ceiling 19. In FIG. 5, the setting bolt 3 is already set in the concrete ceiling 19 and, by means of the retaining part 4, a pull-out force can be applied, as a tubular retaining sleeve 5, on the setting bolt 3. The retaining part 4 has a connecting opening 20 and the diameter of the connecting opening 20 is smaller than the diameter of a carrying ring 28 on one of the axial ends of the setting bolt 3 lying opposite the tip of the setting bolt 3. When using a washer, a larger diameter for the connecting opening is also possible.

Before the setting of the setting bolt 3, the setting bolt 3 is situated within an interior space 29 (FIG. 4) enclosed by the retaining sleeve 5, and after the setting of the setting bolt 3, the setting bolt 3 is essentially situated outside the interior space 29 enclosed by the retaining sleeve 5, and only an end area with the carrying ring 28 remains in the interior space 29. By the application of a pull-out force downwards onto the union nut 150, a pull-out force can thus be applied on the setting bolt 3, since this is transmitted from the remaining pull-out tester 1 onto the retaining sleeve 5 and from the retaining sleeve 5 onto the setting bolt 3.

On the pull-out tester housing 15, two levers 11 are supported, as a transmission site 10, so they can swivel around a swivel axle 12. The two levers 11 are thereby mechanically and kinematically connected with an elastic element 7 as a rotational spring 8 made of metal. Each of the two levers 11 is correlated with a rotational spring 8, so that a swiveling movement of the lever 11 causes an elastic rotational deformation of the rotational spring 8. A support ring 30 is formed on the axial end of the retaining sleeve 5, which is shown below in FIGS. 4 and 5 and which is formed opposite the connecting opening 20. After the setting of the setting bolt 3 and also the movement out of the retaining sleeve 5 from the bolt chamber 27, the support ring 30 lies on two connecting arms 14 as connecting parts 13. The pull-out force acting on the setting bolt 3, which is also connected to the retaining sleeve 5, thus causes a transmission of this force onto the two levers 11, since the two connecting arms 14 lie on the levers 11. The two rotational springs 8 thereby bring a force onto the levers 11, which is directed contrary to the swivel movement of the levers 11, with a swivel movement of the levers 11 around the swivel axle 12. Thus, the greater the pull-out force acting on the setting bolts 3, the greater is the swivel movement of the levers 11 around the swivel axle 12. The connecting arms 14 are thereby also moved with the levers 11 because of a corresponding connection, so that beyond a limiting swivel position of the levers 11, the form-locking connection between the support ring 30 of the retaining sleeve 5 and the two connecting arms 14 is detached, since because of the swivel movement of the levers 11, this swivel movement also causes a radial movement outwards relative to a longitudinal axis of the pull-out tester 1 and thus the connecting arms 14 no longer lie on the support ring 30 of the retaining sleeve 5.

The mechanism or the kinematic system of the pull-out tester 1 is designed to the effect that with a pull-out test force of 0.05 kN, 0.1 kN, 0.15 kN, 0.3 kN, or 0.5 kN acting on the setting bolt 3, the form-locking connection between the connecting arms 14 and the support ring 30 on the retaining sleeve 5 is detached. In this way, the remaining pull-out tester 1 can be moved away from the retaining sleeve 5, so that only the setting bolt 3 with the retaining sleeve 5 still remains on the concrete ceiling 19. If the pull-out force that can be accepted by the setting bolt 3 is smaller than the pull-out force of, for example, 0.15 kN, then the setting bolt 3 is pulled out of the concrete ceiling 19, so that a setting failure of the setting bolt 3 occurs and this unsuitable setting bolt 3 is also pulled out from the concrete ceiling 19. The levers 11 and the two connecting arms 14 thus represent a means 9 for the transmission of a force, as a tensile force on the setting bolt 3, onto the elastic element 7 as a rotational spring 8. The elastic deformation—that is, the elastic rotational movement of the rotational spring 8—is thereby essentially not dependent on the temperature and is also not dependent on the pull-out speed with the pull-out tester 1. The rotational spring 8 is formed from metal, so that, in this way, the spring constant of the rotational spring 8 is essentially constant even at various temperatures. In particular, the rotational spring 8 is thereby formed as a steel spring. The pull-out force that is applied on the setting bolt 3 is either applied by the muscle force of a user, for example, on the retaining rod 25, since the pull-out tester 1 is connected with the remaining setting tool 2, or the pull-out force is applied after or during the setting of the setting bolt 3, or a combination of both, as a result of a return of the setting tool 2.

FIGS. 7 to 9 show a second embodiment of the pull-out tester 1. Below, essentially only the differences with respect to the first embodiment example in accordance with FIGS. 1 to 5 are described. Before the setting of the setting bolt 3, the setting bolt 3 with the bolt chamber 27 is situated on the pull-out tester housing 15, and an essentially U-shaped retaining clip 6 made of metal, in particular, steel, lies on an indirect stop 17 of the pull-out tester housing 15 (FIG. 8). The retaining clip 6 has a locking pin 32 on an end area opposite the connecting opening 20 of the retaining clip 6, as a retaining part 4. During the setting of the setting bolt 3 by means of the setting tool 2, the setting bolt 3 is moved out of the bolt chamber 27 and driven into the concrete ceiling 19 (FIG. 9). Furthermore, as a result of the support ring 28, the retaining clip 6 is also moved from the position shown in FIG. 8 in the direction of the concrete ceiling 19, so that during this movement, the locking pin 32 is moved on a sliding surface 31 of the pull-out tester housing 15 up to a form-locking configuration 21 as a projection 22. In the second embodiment example, the retaining clip 6 thus forms both the retaining part 4 as well as the means 9 for the transmission of the pull-out force acting on the setting bolt 3. Moreover, the retaining clip 6 also forms the elastic element 7 as a spring made of steel.

In the position of the retaining clip 6 shown in FIG. 9, a tensile force can be brought from the projection 22 of the pull-out tester housing 15 onto the locking pin 32, since the retaining clip 6 also forms an elastic element 7 as a spring and the two locking pins 32 on the projection 22 lie under a compression force. Thus, a form-locking and force-locking connection is available between the retaining clip 6 and the pull-out tester housing 15. The retaining clip 6 thereby has an inclined section 23 in the area of the locking pin 32, so that the greater the tensile force transmitted onto the setting bolt 3 by means of the retaining clip 6, the [more] the locking pins 32 of the retaining clip 6 are moved radially against an elastic spring effect of the retaining clip 6, so that beyond a pull-out test force of, for example, 0.15 kN, the locking pins 32 slide off of the form-locking configuration 21 and thus, the pull-out tester housing 15 can be removed from the retaining clip 6 on the setting bolt 3. As a result of the formation of the retaining element 6 out of steel, the pull-out test force of 0.15 kN is essentially constant at various temperatures.

The retaining sleeve 5 in the first embodiment example and also the retaining clip 6 in the second embodiment example can be removed from the setting bolt 3 after a successful pull-out test—that is, the removal of the pull-out tester 5, so that only the setting bolt 3 with the retaining part 4 remains on the concrete ceiling 19. To this end, the retaining part 4 has a corresponding labyrinth so that, in this way, after the pull-out test, the retaining part 4 can be removed from the setting bolt 3 to the extent required. Preferably, however, the retaining part 4 also remains on the setting bolt 3 after the successful pull-out test.

Considered as a whole, substantial advantages are connected with the pull-out tester 1 in accordance with the invention and the setting tool 2 in accordance with the invention. The pull-out tester 1 is built on the setting tool 2.

After the setting of the setting bolt 3, the pull-out force that can be accepted by the setting bolt 3 can be checked or tested with the pull-out tester 1, so that the setting bolt 3 is removed from the concrete ceiling 19 with a pull-out test force smaller than the one specified, for example, 0.15 kN, and thus, a setting failure can be simply and reliably recognized. With a pull-out force of the setting bolt 3 that is acceptable by it and that is greater than the pull-out test force of 0.15 kN, the setting bolt 3 remains in the setting object 18, since beyond the pull-out test force of 0.15 kN, the connection between the setting bolt 3 and the pull-out tester 1—that is, between the retaining part 4 and the remaining pull-out tester 1, in particular, the pull-out tester housing 15—is detached. The pull-out test force is thereby not essentially dependent on the ambient temperature and the pull-out test speed of the pull-out tester housing 15 away from the concrete ceiling 19, since the elastic deformation of the elastic element 7 made of metal, in particular, steel, is not essentially dependent on the temperature and the deformation speed.

The invention claimed is:

1. A setting tool, comprising a housing, a device which sets a setting bolt into a setting object when activated and which has a driving ram and a means for driving the driving ram, a switch which actuates the device, and,
   a pull-out tester which comprises
   a retaining part for retaining the setting bolt,
   an elastic element,
   at least one transmission part for transmission of a pull-out force acting on the setting bolt onto the elastic element, wherein exceeding of a pull-out test force acting on the setting bolt detaches a connection between the setting bolt and the pull-out tester due to deformation of the elastic element.

2. The setting tool according to claim 1, wherein the elastic element of the pull-out tester is a spring and/or the retaining part is a retaining sleeve.

3. The setting tool according to claim 1, wherein the retaining part of the pull-out tester is mechanically connected with the transmission part with at least one connecting part, so that the pull-out force is transmitted from the retaining part onto the transmission part with the at least one connecting part and/or the transmission part and/or the connecting part transmits the pull-out force acting on the setting bolt onto the elastic element.

4. The setting tool according to claim 1, wherein the retaining part of the pull-out tester forms the elastic element and/or the retaining part transmitting the pull-out force acting on the setting bolt onto the elastic element and/or the retaining part is formed as a U-shaped retaining clip.

5. The setting tool according to claim 1, wherein the pull-out tester comprises a form-locking configuration on which the retaining part is fastened in a form-locking manner to provide a form-locking connection, wherein the form-locking connection is detached when the pull-out test force is exceeded.

6. The setting tool according to claim 1, wherein the elastic element of the pull-out tester comprises metal.

7. The setting tool according to claim 6, wherein the elastic element of the pull-out tester is a spring and/or the retaining part is a retaining sleeve.

8. The setting tool according to claim 1, wherein the transmission part is mechanically connected with the retaining part.

9. The setting tool of claim 8, wherein a retaining force on the retaining part acts on the transmission part and deforms the elastic element.

10. The setting tool according to claim 1, wherein
the deformation of the elastic element of the pull-out tester is a completely elastic deformation.

11. The setting tool according to claim 10, wherein the elastic element of the pull-out tester is a spring and/or the retaining part is a retaining sleeve.

12. The setting tool according to claim 10, wherein
the elastic element of the pull-out tester comprises metal.

13. The setting tool according to claim 12, wherein the elastic element of the pull-out tester is a spring and/or the retaining part is a retaining sleeve.

14. A setting tool comprising a housing, a device which sets a setting bolt into a setting object when activated and which has a driving ram and a means for driving the driving ram, a switch which actuates the device, and,
a pull-out tester which comprises
an elastic element;
a retaining part for retaining the setting bolt;
a transmission part mechanically connected with the retaining part and adapted to transmit a pull-out force acting onto the setting bolt onto the elastic element, wherein the transmission part comprises a lever and a retaining force on the retaining part acts on the transmission part and deforms the elastic element.

* * * * *